(12) United States Patent
Hammon et al.

(10) Patent No.: US 10,343,969 B2
(45) Date of Patent: Jul. 9, 2019

(54) PROCESS AND PLANT FOR RECOVERING ACRYLIC ACID

(71) Applicant: BASF SE, Ludwigshafen (DE)

(72) Inventors: Ulrich Hammon, Mannheim (DE); Thomas Walter, Hassloch (DE); Markus Ottenbacher, Wilhelmsfeld (DE); Frank Huetten, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/615,852

(22) Filed: Jun. 7, 2017

(65) Prior Publication Data
US 2017/0267621 A1  Sep. 21, 2017

Related U.S. Application Data

(62) Division of application No. 14/857,967, filed on Sep. 18, 2015, now Pat. No. 9,701,612.
(Continued)

(30) Foreign Application Priority Data

Sep. 30, 2014  (DE) .................. 10 2014 114 193

(51) Int. Cl.
*B01J 19/24* (2006.01)
*C07C 51/487* (2006.01)
(Continued)

(52) U.S. Cl.
CPC ............ *C07C 51/487* (2013.01); *B01D 3/009* (2013.01); *B01D 3/143* (2013.01); *B01D 3/346* (2013.01);
(Continued)

(58) Field of Classification Search
CPC ........................................................ B01J 19/24
See application file for complete search history.

(56) References Cited

U.S. PATENT DOCUMENTS 6,482,981 B2 * 11/2002 Ueno .................... C07C 51/252
562/532
6,679,939 B1   1/2004 Thiel et al.
(Continued)

FOREIGN PATENT DOCUMENTS

DE        199 24 533 A1   11/2000
DE        102 47 240 A1    4/2004
DE   10 2007 055 086 A1    5/2009

OTHER PUBLICATIONS

Lee et al. Optimize Design for Distillation Feed. GTC Technology. Jun. 2011. (Year: 2011).*

*Primary Examiner* — Donald R Spamer
(74) *Attorney, Agent, or Firm* — Oblon, McClelland, Maier & Neustadt, L.L.P.

(57) ABSTRACT

A plant (1) for recovering acrylic acid, which includes: a absorption column (201); a dissociation column (205); a first line (101) connected to the dissociation column (205); a second line (102) connecting the absorption column (201) and the dissociation column (205); a third line (103) feeding a substream of the mother acid obtained in the crystallization into the dissociation column (205); a fourth line (104) connecting the crystallization apparatus and the absorption column (201); and a fifth line (105) connecting the dissociation column (205) and the absorption column (201).

6 Claims, 1 Drawing Sheet

Related U.S. Application Data

(60) Provisional application No. 62/057,267, filed on Sep. 30, 2014.

(51) Int. Cl.
*C07C 51/44* (2006.01)
*C07C 51/48* (2006.01)
*B01D 3/34* (2006.01)
*B01D 3/00* (2006.01)
*B01D 3/14* (2006.01)
*C07C 51/42* (2006.01)
*C07C 57/04* (2006.01)

(52) U.S. Cl.
CPC ............... *B01J 19/24* (2013.01); *C07C 51/42* (2013.01); *C07C 51/44* (2013.01); *C07C 51/48* (2013.01); *C07C 57/04* (2013.01); *B01J 2219/24* (2013.01)

(56) References Cited

U.S. PATENT DOCUMENTS

| | | |
|---|---|---|
| 6,939,991 B2 | 9/2005 | Thiel et al. |
| 7,566,804 B2 | 7/2009 | Diefenbacher et al. |
| 2004/0073063 A1* | 4/2004 | Thiel ............... C07C 51/44 562/545 |
| 2004/0249199 A1* | 12/2004 | Ueno ............... C07C 51/43 562/545 |
| 2008/0071111 A1* | 3/2008 | Nakagawa ............... C07C 51/42 562/600 |
| 2012/0071620 A1* | 3/2012 | Sakamoto ............... C07C 51/43 526/317.1 |

\* cited by examiner

PROCESS AND PLANT FOR RECOVERING ACRYLIC ACID

This patent application is a divisional of U.S. patent application Ser. No. 14/857,967 (now U.S. Pat. No. 9,701,612), filed on Sep. 18, 2015, which claims the benefit of U.S. provisional patent application Ser. No. 62/057,267 and DE patent application Serial Number DE 10 2014 114 193.8, both filed on Sep. 30, 2014, incorporated in their entirety herein by reference.

The present invention relates to a process and a plant for recovering acrylic acid.

Acrylic acid is an important basic chemical. Owing to its very reactive double bond and also the acid function, it is, in particular as monomer, suitable for preparing polymers. Of the amount of acrylic acid monomer produced, the major part is, for example, esterified before polymerization (e.g. to give adhesives, dispersions or surface coating compositions). Only a minor part is polymerized directly (e.g. to give "superabsorbents"). While monomer of high purity is generally required in the direct polymerization of acrylic acid, the requirements in respect of the purity of the acrylic acid are not as demanding when it is esterified before polymerization.

Acrylic acid can be obtained, inter alia, by heterogeneously catalyzed gas-phase partial oxidation of $C_3$ precursors of acrylic acid by means of molecular oxygen over solid-state catalysts at elevated temperature. The term $C_3$ precursors encompasses chemical compounds which are formally obtainable by reduction of acrylic acid. In the preparative process, these $C_3$ precursors are passed in the gaseous state, generally diluted with inert gases such as nitrogen, $CO_2$, saturated hydrocarbons and/or steam, in a mixture with molecular oxygen at elevated temperatures and optionally superatmospheric pressure over transition metal mixed oxide catalysts and oxidatively converted into a product gas mixture which comprises acrylic acid and secondary components such as furfurals, benzaldehyde and maleic anhydride and from which the acrylic acid has to be separated off.

The acrylic acid obtained is not a pure product but instead a mixture comprising not only acrylic acid (in general ≥90%, or ≥95% of the total weight) but also typical by-products of the gas-phase oxidation, e.g. water, lower aldehydes (e.g. furfurals, acroleins or methacrolein, benzaldehyde), lower carboxylic acids (e.g. acetic acid, propionoic acid), etc., and oligomers of acrylic acid.

The cause of the formation of oligomers of acrylic acid is that acrylic acid present in the condensed phase forms acrylic acid oligomers (Michael adducts) by reversible Michael addition onto itself and onto the dimer which is formed, and also oligomers formed by free-radical polymerization. The presence of water, the unavoidable by-product of a gas-phase catalytic oxidative preparation of acrylic acid, and elevated temperatures promote the formation of oligomers of acrylic acid.

Since the respective oligomers have a higher boiling point than acrylic acid, they accumulate in the high boiler fraction (e.g. in the liquid bottoms) both in an isolation of acrylic acid by distillation and in a fractional condensation of the product gas mixture from a gas-phase catalytic oxidative preparation.

DE 199 24 533 A1 discloses a process as described above for preparing acrylic acid, in which a basic isolation of a crude acrylic acid is carried out by fractional condensation of the product gas mixture from the heterogeneously catalyzed gas-phase partial oxidation. A redissociation of the acrylic acid oligomers comprised in the output of a quenching liquid is said to be integrated in such a way that the time on stream of the process, in particular of the fractional condensation, is not decreased significantly. The redissociation of the acrylic acid oligomers has the aim of increasing the yield of product of value. DE 199 24 533 A1 provides a circulation reactor for the dissociation.

DE 102 47 240 A1 describes a very similar process for preparing acrylic acid, in which a product gas mixture comprising acrylic acid is firstly cooled by direct cooling with a quenching liquid and the cooled product gas mixture is subsequently fed into a condensation column equipped with separation-active internals. The crude acrylic acid is taken off from the condensation column and passed to a further purification by crystallization. The mother liquor obtained in this purification by crystallization is recirculated in its entirety to the condensation column. Liquid bottoms comprising acrylic acid oligomers are taken from the bottom of the condensation column and used as quenching liquid. The part of the quenching liquid which is not vaporized during cooling of the product gas mixture is circulated via the bottom and optionally via a heat exchanger and part of the quenching liquid is discharged as output from this circuit and fed to a dissociation vessel for redissociation. The acrylic acid-comprising dissociation gases which are given off in gaseous form are recirculated to the circuit of the quenching liquid or to the condensation column or to the circuit of the quenching liquid and to the condensation column, with the dissociation gases being subjected to a countercurrent rectification and at least partial condensation before being recirculated; here, the amount of condensate formed corresponds to at least the amount of runback necessary for the countercurrent rectification.

The processes according to the prior art are in themselves advantageous and lead to appropriate yields of product of value, i.e. of acrylic acid. However, these increased yields are made possible only by means of a high outlay in terms of apparatus and energy consumption.

In view of this background, it is an object of the present invention to indicate a process for recovering acrylic acid and provide a corresponding plant, the two of which increase the yield of product of value further compared to the prior art but at the same time allow the process to be carried out more efficiently in respect of the outlay in terms of apparatus and energy.

The above object is achieved, in a first aspect of the present invention, by a process for recovering acrylic acid, which comprises the steps of
a) division of a heated mother acid stream from a crystallization apparatus in the direction of an absorption column (201) and in the direction of a dissociation column (205),
b) feeding of the first heated mother acid substream as runback to the uppermost tray of the dissociation column (205),
c) feeding-in of at least one stripping gas stream below the lowermost tray of the dissociation column (205),
d) feeding-in of a secondary component stream comprising oligomeric acrylic acid from the absorption column (201) to a middle tray of the dissociation column (205),
e) dissociation of at least part of the oligomeric acrylic acid from the secondary component stream in the dissociation column (205) to give monomeric acrylic acid, removal of the secondary components comprised in the secondary component stream by countercurrent rectification in the superposed dissociation column (205), g) discharge of the monomeric acrylic acid without condensation as gas mixture with the introduced circulating stripping gas stream at the top of the dissociation column (205) and h) feeding-in of the gas mixture below the lowermost tray of the absorption column (201).

In a second aspect of the present invention, the above object is achieved by a plant (I) for recovering acrylic acid, which comprises a absorption column (201), a dissociation column (205), a first line (101) connected to the dissociation column (205), a second line (102) connecting the absorption column (201) and the dissociation column (205), a third line (103) feeding a substream of the mother acid obtained in the crystallization into the dissociation column (205), a fourth line (104) connecting the crystallization apparatus and the absorption column (201) and a fifth line (105) connecting the dissociation column (205) and the absorption column (201).

The present invention has the substantial advantage that the process of the invention and the plant (1) of the invention allow secondary components formed in the preparation of acrylic acid, in particular oligomeric acrylic acid, to be dissociated and recirculated with improved efficiently to the preparative process, as a result of which the yield of product of value, i.e. of acrylic acid, and its purity can be increased.

The present invention is described in detail below.

Where reference is made to process features in the context of the plant (1) of the invention in the description below, these preferably relate to the process of the invention. Likewise, substantive features which can be carried out in the context of the process of the invention preferably relate to the plant (1) of the invention.

In a first aspect of the present invention, the abovementioned object is achieved by a process for recovering acrylic acid. The process of the invention comprises the steps a) to h) and is described below.

In a step a), a heated mother acid stream from a crystallization apparatus is divided into two substreams in the direction of an absorption column (201) and in the direction of a dissociation column (205). For the purposes of the present invention, "heated" means that the mother acid stream or the mother acid substreams has/have, after discharge from the crystallization apparatus, been heated to a temperature of preferably from 50° C. to 100° C., more preferably from 60° C. to 90° C., in particular from 70° C. to 80° C. The configuration according to the invention of the process is not limited to a particular crystallization process by means of which acrylic acid is purified by partial crystallization, separation of the frozen-out acrylic acid from the liquid (mother acid) comprising the impurities and melting of the pure acrylic acid crystals which have been separated off. Here, for example, it is possible to use a falling film crystallization or a suspension crystallization as combination of cooling plate crystallizers and scrubbing columns, with the latter process variant being preferred.

In the context of the present invention, the term "mother acid" (in comparable documents sometimes also referred to as "mother liquor") refers to a solution of acrylic acid which, after the pure product has been separated off in a crystallization apparatus, comprises the impurities separated off in the crystallization apparatus, with the proportion by weight of acrylic acid in the mother acid being ≥80% by weight.

In step b), a first heated mother acid substream is fed to the uppermost tray of the dissociation column (205) having 45 trays. The dissociation column (205) is, according to the present invention, preferably equipped with dual-flow trays as separation-effective internals. A second heated mother acid substream is introduced onto tray 18 of the absorption column (201) comprising 75 trays.

A step c) provides for introduction of at least one stripping gas stream below the uppermost tray of the dissociation column (205). Here, the stripping gas stream is preferably directed onto the liquid surface of the liquid phase. The stripping gas stream is, in particular, used as circulating gas. For the purposes of the present invention, "circulating gas" is a gas which serves for dilution of the starting materials and uptake of heat of reaction in the gas-phase oxidation and is essentially inert in the gas-phase reaction. The circulating gas comprises essentially nitrogen and, at a concentration of <5% by volume, oxygen, water vapor, carbon oxides and mixtures thereof and very small amounts (<0.8% by volume) of ethylene, ethane, propene, propane, acrolein, acrylic acid and acetic acid.

In a step d), a secondary component stream comprising oligomeric acrylic acid from the absorption column (201) is fed to a middle tray of the dissociation column (205). This middle tray is, in particular, a tray in the tray region 8 and 10.

In a step e), at least part of the oligomeric acrylic acid in the secondary component stream is dissociated in the dissociation column (205) to give monomeric acrylic acid. This preferably occurs thermally at temperatures of >150° C. The dissociation can be accelerated by addition of small amounts of sodium hydroxide or amines to the liquid phase in the dissociation column.

Step f) provides for removal of the secondary components comprised in the secondary component stream by countercurrent rectification in the superposed dissociation column (205).

The monomeric acrylic acid obtained in step e) is, in a step g), discharged without condensation as gas mixture together with the introduced circulating stripping gas stream at the top of the dissociation column (205) and the gas mixture is subsequently, in a step h), fed in below the uppermost tray of the absorption column (201).

The monomeric acrylic acid is thus recirculated to the process in an advantageous way. Since the acrylic acid is introduced in gaseous form and does not have to be vaporized first there, more energy is available for separation of the acrylic acid from secondary components in the absorption column (201). According to the present invention, the absorption column (201) is preferably configured as a tray column. It is preferably equipped with dual-flow trays in the lower region, with Thormann trays in the middle region and with valve trays in the upper region.

The process of the invention has the advantage over the prior art that partial condensation of the acrylic acid stripped out in the dissociation column (205) to provide runback for the rectification column is dispensed with and part of the molar acid stream produced in the crystallization apparatus is used instead of the runback produced by condensation of the vapor at the top of the dissociation column (205). As a result, a condensation unit at the top of the dissociation column (205) can be omitted, which reduces the outlay in terms of apparatus. In addition, it is not necessary to provide cooling power for condensation. Furthermore, the energy introduced via a bottom heat exchanger of the dissociation column (205) is additionally available in the absorption column (201), which improves the separation of acrylic acid from secondary components.

A further advantage of the present process is that monomeric acrylic acid can be recovered in an improved yield from the respective oligomers by means of the process of the invention and can be returned as low boiler to the overall process. The term "oligomeric acrylic acid" refers, in particular, to dimers and trimers of acrylic acid. Compared to the prior art, the work-up loss of acrylic acid is reduced by 0.3%. For the purposes of the present patent application, the term "work-up loss" refers to the proportion of acrylic acid which, based on the acrylic acid supplied from the synthesis, is not separated off from the secondary components and cannot be obtained as product.

The process of the invention can advantageously be carried out by means of a plant (1) according to the invention, which is described below.

In an embodiment of the process of the invention, it has been found to be advantageous for the mother acid stream to be heated, in particular, against an acrylic acid stream from a absorption column (201). The acrylic acid stream is preferably taken off as target product via a side offtake of the absorption column (201) and essentially fed to a crystallization apparatus. This acrylic acid stream is hot (i.e. from 95° C. to 100° C.) and highly concentrated (i.e. from 95% by weight to 98% by weight of acrylic acid) and has to be cooled before entering the crystallization apparatus.

According to the invention, the heat energy present in the acrylic acid stream is therefore transferred by means of a heat exchanger to the mother acid stream and thus introduced into the two mother acid substreams. This energy is thus available both in the absorption column (201) for fractionation of the acrylic acid and in the dissociation column (205) for dissociation of the dimeric acrylic acid, or less energy has to be introduced into the dissociation via a bottom heat exchanger present on the dissociation column (205).

In a preferred embodiment, step h) is carried out indirectly by the gas mixture being introduced into a quenching apparatus (203) for quenching a product gas mixture comprising acrylic acid.

The mother acid stream taken off from the crystallization apparatus preferably comprises essentially acrylic acid and proportions of water and acetic acid, in particular from 90% by weight to 95% by weight of acrylic acid, from 3% by weight to 6% by weight of water and from 1% by weight to 2% by weight of acetic acid and also small proportions (in each case <0.5% by weight) of formaldehyde, propionoic acid, furfural, maleic acid and diacrylic acid. The mother acid stream is taken off with a temperature just above the crystallization temperature of acrylic acid (from 15° C. to 20° C.) and preferably preheated to the corresponding thermodynamic equilibrium temperature at the position of the point of introduction into the absorption column (201) of about 80° C. in order to ensure very effective separation.

Furthermore, the secondary component stream preferably comprises essentially acrylic acid, diacrylic acid and polyacrylic acid and also proportions of maleic acid, benzoic acid, benzaldehyde, furfurals and water, in particular from 50% by weight to 60% by weight of acrylic acid or methacrylic acid, from 20% by weight to 30% by weight of diacrylic acid and from 5% by weight to 10% by weight of polyacrylic acid and also from 6% by weight to 9% by weight of maleic acid, from 1% by weight to 2% by weight of benzoic acid, from 0.5% by weight to 1% by weight of water and from 0.5% by weight to 1% by weight of 4-methoxyphenol, also small proportions (in each case <0.5% by weight) of acetic acid, furfural, benzaldehyde, phthalic anhydride, phenothiazine and diacrylic acid. The secondary component stream preferably has a temperature of from 100° C. to 130° C., in particular from 105° C. to 115° C., in order firstly to achieve sufficient preconcentration of the bottom liquid from the absorption column (201) before transfer into the dissociation column (205) and secondly to limit dimer formation in the bottom region of the absorption column (201).

In addition, the stripping gas stream can comprise essentially nitrogen, acrylic acid, water and oxygen and also proportions of carbon dioxide and acetic acid, in particular from 80% by weight to 85% by weight of nitrogen, from 3% by weight to 5% by weight of acrylic acid, from 3% by weight to 5% by weight of water, from 3% by weight to 4% by weight of oxygen, from 2% by weight to 3% by weight of carbon dioxide and from 1% by weight to 2% by weight of acetic acid and also small proportions (in each case <0.7% by weight) of carbon monoxide, acrolein or methacrolein, formic acid, propene and propane. The stripping gas stream preferably has a temperature of from 80° C. to 90° C., in particular about 85° C.

It has been found to be advantageous in terms of the efficiency of the process of the invention, in particular for the yield of product of value, for from 60% to 95%, in particular from 85% to 90%, of the dissociable components of the secondary component stream to be dissociated in step e). Preference is given to essentially the dimers and trimers of acrylic acid being dissociated. As regards the yields of product of value, higher degrees of dissociation of 95% are advantageous, but are technically difficult to control since at dissociation yields of >95% the remaining product tends to undergo massive solids formation and is thus very difficult to handle.

In a second aspect of the present invention, the above-mentioned object is achieved by a plant (1) for recovering acrylic acid. The plant (1) according to the invention comprises a absorption column (201) and a dissociation column (205).

What is meant by the absorption column (201) and the dissociation column (205) for the purposes of the present invention has been described above in relation to the process of the invention.

The plant (1) further comprises a first line (101) which is connected to the dissociation column (205) and feeds at least one gas stream as circulating stripping gas to the bottom region of the dissociation column (205). A second line (102) connects the absorption column (201) and the dissociation column (205) and conveys a secondary component stream from the absorption column (201) to the dissociation column (205).

A third line (103) serves for transfer of a substream of the mother acid obtained in the crystallization to the dissociation column (205). A crystallization apparatus and the absorption column (201) are connected by a fourth line (104) and the dissociation column (205) and the absorption column (201) are connected by a fifth line (105).

Corresponding definitions of the elements of the plant (1) and terms used have been given above in relation to the process of the invention and also apply to this plant (1).

The advantages of the plant (1) of the invention are essentially the same as for the above-described process of the invention. The present plant (1) creates the prerequisites in terms of apparatus for dividing the mother acid stream to give two mother acid substreams and feed these to the absorption column (201) and the dissociation column (205).

In this way, no energy is taken off from the overall process but instead remains in the process. The provision of additional heat exchangers for introduction of external energy is greatly reduced.

In addition, plant parts and apparatuses provided in plants of the type in question in the prior art can be saved, for example surface condensers or spray condensers with associated pumps and heat exchangers, also devices for metering in inhibitors. In ongoing operation of the plant, the amounts of inhibitors for avoiding polymerization of acrylic acid can be reduced since the use of mother acid as runback to the dissociation column (205) already provides a sufficiently stabilized acrylic acid.

In an embodiment of the plant (1) of the invention, this plant further comprises a quenching apparatus (203) for quenching a product gas mixture comprising acrylic acid, which is arranged in the fifth line (105) between the dissociation column (205) and the absorption column (201). This provides a physical means of efficiently exploiting the gas mixture from the dissociation column (205) and its temperature for quenching the hot product gas mixture.

The plant (1) of the invention is particularly advantageous when it is integrated into an overall plant for the preparation of acrylic acid. As indicated above, the plant (1) of the invention can increase the total efficiency of acrylic acid production while at the same time reducing the outlay in terms of apparatus.

Further objectives, features, advantages and possible uses can be derived from the following description of examples of the invention with the aid of the FIGURE. Here, all features described and/or depicted form, in themselves or in any combination, the subject matter of the invention, even independently of their summary in the claims or their back-reference. The drawing shows:

Figure 1:
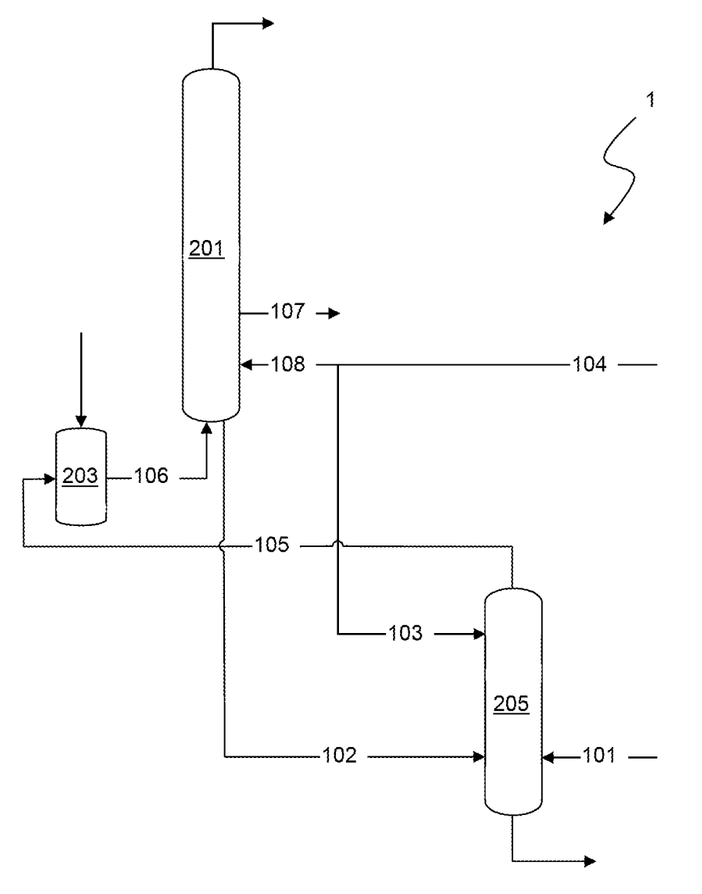
FIG. 1 a schematic depiction of the plant 1 according to the invention in one embodiment of the invention.

FIG. 1 schematically shows the plant 1 according to the invention in one embodiment of the invention. Central elements here are the absorption column 201 and the dissociation column 205.

From a part of the plant which is not shown and in which the heterogeneously catalyzed gas-phase partial oxidation is carried out, a hot product gas stream is fed in with a temperature of about 270° C. This is introduced into a quenching apparatus 203 in order to suppress possible reactions of its constituents and to reduce its temperature. A gas mixture from the dissociation column 205 having a temperature of about 95° C. is likewise fed via a fifth line 105 into the quenching apparatus 203. This gas mixture will be described in more detail later.

The gases and liquids fed into the quenching apparatus 203 are, after leaving the latter, fed into the bottom region of the absorption column 201. In this absorption column 201, the acrylic acid produced is separated off from the product mixture by absorption and taken off from the absorption column 201 via a side offtake. The acrylic acid stream taken off is highly concentrated (about 97% of acrylic acid) and has a temperature of about 99° C. This acrylic acid stream (also referred to as "crude acrylic acid") is fed via a series of apparatuses which will not be described in more detail here to a crystallization apparatus in which purification of the acrylic acid by crystallization is carried out. Apart from highly pure crystalline acrylic acid, mother acid also remains in the crystallization apparatus and this is taken off as mother acid stream via a line 104.

While according to the prior art (see, for example, DE 102 47 240 A1) this mother acid stream is fed directly to a lower tray of an absorption column (comparable to absorption column 201), it is a feature of the invention that the mother acid stream is thermally coupled against the acrylic acid stream taken off the absorption column 201. The mother acid stream initially has a temperature of about 20° C. and is heated to about 93° C. by the thermal coupling. In this way, the excess heat energy of the acrylic acid stream can be transferred to the mother acid stream.

The heated mother acid stream is divided into a first mother acid substream and a second mother acid substream. While the second mother acid substream is fed via line 108 to the absorption column 201, the first mother acid substream is fed as runback via a third line 103 to the uppermost tray of the dissociation column 205 and the heat energy of the acrylic acid stream is thus indirectly introduced into the dissociation reaction.

The dissociation column 205 is supplied via a first line 101 with a stripping gas stream as circulating gas from a plant section, which will not be described in more detail, below the lowermost tray. This stripping gas stream has a temperature of about 85° C. At a middle tray of the dissociation column 205, a secondary component stream comprising oligomeric acrylic acid and having a temperature of about 109° C. is fed in via a second line 102 from the bottom of the absorption column 201.

The secondary component stream comprises high boilers such as benzaldehyde, furfural and maleic acid. However, the major constituent of the secondary component stream is acrylic acid together with oligomers thereof and polyacrylic acid.

These secondary components, in particular the acrylic acid oligomers, are redissociated in the dissociation column 205 and taken off as low boiler fraction together with the circulating gas via the top of the column. This low boiler fraction forms the gas mixture and is fed via line 105 to the quenching apparatus 203. The high-boiling components, in particular, remain in the bottom of the dissociation column 205 and are taken off and passed to disposal.

In the present example, the yield of acrylic acid as product of value is significantly increased by redissociation of the acrylic acid oligomers and recirculation to the absorption column 201. The process of the invention and the plant 1 according to the invention make it possible to produce an amount of 20.4 t/h of acrylic acid.

A specific embodiment is described below for the example of the preparation of acrylic acid.

EXAMPLE (THE STEADY STATE IS DESCRIBED)

A heterogeneously catalyzed gas-phase oxidation of propylene of "polymer grade" purity gave a product gas mixture having a temperature of 301° C. and the following composition:

12.168% by weight of acrylic acid,
0.242% by weight of acetic acid,
5.281% by weight of water,
0.035% by weight of formic acid,
0.18% by weight of formaldehyde,
0.068% by weight of acrolein,
0.005% by weight of propionoic acid,
0.003% by weight of furfurals,
0.001% by weight of allyl acrylate,
0.0005% by weight of allyl formate,
0.013% by weight of benzaldehyde,
0.148% by weight of maleic anhydride,
0.011% by weight of benzoic acid, 0.011% by weight of phthalic anhydride,
2.126% by weight of $CO_2$,
0.658% by weight of CO,
0.08% by weight of propane,
0.174% by weight of propylene,
3.06% by weight of oxygen and
75.728% by weight of nitrogen.
Further constituents are not detected.

The product gas mixture (176 610 kg/h) is cooled to a temperature of 120.1° C. by direct cooling in a spray cooler operated cocurrently. The liquid used for the direct cooling is a mixture of bottom liquid from the absorption column 201 and high boiler fraction taken off from the first collection tray closing off the bottom region of this absorption column 201. The composition of the bottom liquid is:

35.59% by weight of acrylic acid,
0.16% by weight of acetic acid,
0.71% by weight of water,
0.01% by weight of formic acid,
<0.001% by weight of formaldehyde,
0.01% by weight of acrolein,
0.04% by weight of propionoic acid,
0.21% by weight of furfurals,
0.001% by weight of allyl acrylate,
<0.001% by weight of allyl formate,
0.68% by weight of benzaldehyde,
10.56% by weight of maleic anhydride,
0.683% by weight of benzoic acid,
0.77% by weight of phthalic anhydride,
41.09% by weight of diacrylic acid,
8.0% by weight of polyacrylic acid (Michael adducts),
0.34% by weight of phenothiazine,
0.82% by weight of MEHQ,
0.59% by weight of other high-boiling constituents and
<0.001% by weight of oxygen.

The high boiler fraction has the following composition:
86.62% by weight of acrylic acid,
0.29% by weight of acetic acid,
1.32% by weight of water,
0.02% by weight of formic acid,
0.002% by weight of formaldehyde,
0.011% by weight of acrolein,
0.09% by weight of propionoic acid,
0.42% by weight of furfurals,
0.002% by weight of allyl acrylate,
0.001% by weight of allyl formate,
1.03% by weight of benzaldehyde,
8.39% by weight of maleic anhydride,
0.03% by weight of benzoic acid,
0.02% by weight of phthalic anhydride,
1.61% by weight of diacrylic acid,
0.017% by weight of phenothiazine,
0.07% by weight of MEHQ and
0.0004% by weight of oxygen.

The amount of the high boiler fraction taken off is 79 528 kg/h. It is taken off at a temperature of 105° C. and fed at this temperature to the spray cooler. The amount of the bottom liquid taken off from the absorption column 201 is 339 150 kg/h. It is taken off at a temperature of 120° C. Only an amount of 336 690 kg/h having this temperature is fed to the spray cooler. 2 460 kg/h are fed to the redissociation.

The mixture of product gas mixture and quenching liquid which results from the direct cooling and has been cooled to 126° C. is fed as such into the bottom of the absorption column 201. The pressure in the bottom region and in the spray cooler is 1.48 bar. The height of the absorption column 201 is 54.3 m.

The internal diameter of the absorption column 201 is 6.5 m in the region of the Thormann trays and otherwise 6.0 m.

2460 kg/h of the bottom liquid taken off are fed to the dissociation column 205 (consisting of a forced circulation flash evaporator and a dual-flow tray rectification column seamlessly joined to the top of this). The number of dual-flow trays is 50. Like the absorption column 201, the dissociation column 205 is insulated from the surroundings. The internal diameter of the dissociation column 205 is uniformly 2.4 m over all dual-flow trays. Its height is 27 m. The dual-flow trays are arranged equidistantly (400 mm) in the dissociation column 205. Their opening ratio is uniformly 12%. Viewed from the bottom upward, the hole diameter of the first eight dual-flow trays is uniformly 25 mm (hole arrangement corresponding to strict triangular distribution) and the hole diameter of all subsequent dual-flow trays is uniformly 14 mm (hole arrangement likewise corresponding to strict triangular distribution). The bottom liquid to be subjected to redissociation is fed in on the eighth dual-flow tray.

19 999 kg/h of a stripping gas stream which has been discharged at the top of the absorption column 201 and subsequently superheated and compressed (pressure: 2.9 bar; temperature: 157° C.) are fed into the bottom of the dissociation column 205. The composition of the stripping gas stream is:

0.269% by weight of acrylic acid,
0.090% by weight of acetic acid,
0.085% by weight of formaldehyde,
2.689% by weight of water,
0.009% by weight of formic acid,
0.08% by weight of acrolein,
0.001% by weight of propionoic acid,
0.001% by weight of furfurals,
0.001% by weight of allyl formate,
3.672% by weight of oxygen,
2.517% by weight of $CO_2$,
0.779% by weight of CO,
0.095% by weight of propane,
0.212% by weight of propylene and
89.5% by weight of nitrogen.

513 646 kg/h of liquid phase having a temperature of 180° C. are continually taken off from the forced circulation flash evaporator. Of this, 512 997 kg/h are recirculated at a temperature of 180° C. to the forced circulation flash evaporator. The other 649 kg/h are degassed, diluted with methanol and passed to a residue incineration.

The dissociation gases formed in the forced circulation flash evaporator are conveyed by means of the introduced stripping gas stream into the superposed rectification column and in this rise through the descending runback liquid.

An amount of 28 523 kg/h of a gas mixture (comprising stripping gas stream and dissociation gas) is discharged (temperature: 91° C., pressure: 1.60 bar) from the top of the rectification column and recirculated to the bottom region of the absorption column 201. The recirculated gas mixture has the following composition:

28.8% by weight of acrylic acid,
0.219% by weight of acetic acid,
2.893% by weight of water,
0.018% by weight of formic acid,
0.081% by weight of formaldehyde,
0.057% by weight of acrolein,
0.041% by weight of propionoic acid,
0.028% by weight of furfurals,
0.001% by weight of allyl acrylate,
0.001% by weight of allyl formate, 0.004% by weight of benzaldehyde,
0.004% by weight of maleic anhydride,
2.54% by weight of oxygen,
1.765% by weight of $CO_2$,
0.546% by weight of CO,
0.066% by weight of propane,
0.149% by weight of propylene and
62.788% by weight of nitrogen.

As runback liquid, 6962 kg/h of mother acid from the crystallization apparatus are recirculated to the uppermost tray of the rectification column comprising 50 trays.

The composition of the mother liquor is:
94.436% by weight of acrylic acid,
0.596% by weight of acetic acid,
3.788% by weight of water,
0.044% by weight of formic acid,
0.005% by weight of acrolein,
0.156% by weight of propionoic acid,
0.127% by weight of furfurals,
0.003% by weight of allyl acrylate,
0.001% by weight of allyl formate,
0.031% by weight of benzaldehyde,
0.040% by weight of maleic anhydride,
0.530% by weight of diacrylic acid,
0.139% by weight of polyacrylic acid (Michael adducts),
0.009% by weight of phenothiazine,
0.022% by weight of MEHQ,
0.072% by weight of other high-boiling constituents and
0.001% by weight of oxygen.

A centrifugal droplet separator is integrated into the bottom region of the absorption column 201 so as to prevent droplets of the bottom liquid being carried out in an upward direction from the bottom region.

The bottom region of the absorption column 201 is, as mentioned above, closed off by a first collection tray (chimney tray having 16 approximately uniformly distributed roofed chimneys; chimney diameter: 600 mm; chimney height: 1 m) at a column height (as in the case of all heights, calculated from the bottom tray upward) of 7.80 m.

The collection tray is configured with two walls and a 2° fall in an inward direction and provided with a central offtake cup and offtake ports (DN-200). The free gas cross section is about 30%. From this first collection tray, 83 559 kg/h of liquid are taken off as mentioned above and fed into the spray cooler.

The temperature at the bottom is 126° C. The pressure is 1.48 bar.

2.0 m above the first collection tray there is the first of initially 15 dual-flow trays. These dual-flow trays (hole diameter uniformly 14 mm, number of holes uniformly 33 678, opening ratio uniformly 18%) are arranged equidistantly with a tray spacing of 380 mm. The through openings consist of circular openings having a uniform diameter of 14 mm, with the stamping flash pointing downward in the separation column. The opening ratio is about 20%. The arrangement of the midpoints of the circular openings follows a strict triangular distribution. The closest distance between two midpoints of circles is 30 mm.

The fifteenth dual-flow tray is configured as a distributor tray. For this purpose, it comprises two plug-in tubes (DN-150) having 40 outflow holes (diameter: 15 mm) per plug-in tube.

The first series of dual-flow trays is ended by a second collection tray (chimney tray having 16 approximately uniformly distributed roofed chimneys; chimney height about 1.70 m, central offtake cup with offtake ports (DN-250), free gas cross section of 30%) which is located 1.50 m above the last dual-flow tray. From this second collection tray, crude acrylic acid having a temperature of 102° C. and the following composition is continuously taken off at 1.47 bar:
97.076% by weight of acrylic acid,
0.4200% by weight of acetic acid,
1.614% by weight of water,
0.021% by weight of formic acid,
0.006% by weight of formaldehyde,
0.004% by weight of acrolein,
0.132% by weight of propionoic acid,
0.100% by weight of furfurals,
0.003% by weight of allyl acrylates,
0.0006% by weight of allyl formate,
0.025% by weight of benzaldehyde,
0.031% by weight of maleic anhydride,
0.543% by weight of diacrylic acid,
0.007% by weight of phenothiazine,
0.017% by weight of MEHQ and
0.0004% by weight of oxygen.

53 766 kg/h of the crude acrylic acid taken off from the second collection tray is recirculated directly to the absorption column 201 at a point below the dual-flow tray following the second collection tray in an upward direction.

91 152 kg/h of the crude acrylic acid taken off from the second collection tray are cooled to a temperature of 29° C. in a plurality of stages by indirect heat exchange (preferably heat-integrated against the mother acid to be recirculated to the absorption column 201). 1694 kg/h of the acidic water obtained at the top of the absorption column 201 are then added to the cooled crude acrylic acid. The resulting mixture is cooled by further indirect heat exchange to 16.4° C. and then fed into two or three cooling plate crystallizers.

After partial crystallization, isolation and melting in hydraulic scrubbing columns, 20 973 kg/h of pure acrylic acid having the following composition are taken off from the crystallization:
99.8247% by weight of acrylic acid,
0.1011% by weight of acetic acid,
0.0210% by weight of water,
0.0377% by weight of propionoic acid,
0.0001% by weight of furfurals,
0.0001% by weight of maleic anhydride,
0.0003% by weight of diacrylic acid and
0.0150% by weight of MEHQ.

It is outstandingly suitable for the production of superabsorbents based on poly-Na-acrylate.

13 kg/h of PTZ are dissolved in 834 kg/h of the pure acrylic acid to produce an inhibitor solution 1. 19 kg/h of MEHQ are dissolved in 30 kg/h of inhibitor solution 1 to form the inhibitor solution 2.

The mother acid separated off in the hydraulic scrubbing columns is firstly fed into a heatable collection vessel and from there into a tank. From this, it is heated by heat integration to 90° C. and recirculated in an amount of 65 038 kg/h to the fifteenth dual-flow tray of the absorption column 201 (counted from the top). The composition of this recirculated mother acid is as follows:
94.436% by weight of acrylic acid,
0.596% by weight of acetic acid,
3.788% by weight of water,
0.044% by weight of formic acid,
0.005% by weight of acrolein,
0.156% by weight of propionoic acid,
0.127% by weight of furfurals,
0.003% by weight of allyl acrylate,
0.001% by weight of allyl formate,
0.031% by weight of benzaldehyde, 0.040% by weight of maleic anhydride,
0.530% by weight of diacrylic acid,
0.139% by weight of polyacrylic acid (Michael adducts),
0.009% by weight of phenothiazine,
0.022% by weight of MEHQ,
0.072% by weight of other high-boiling constituents and
0.001% by weight of oxygen.

2.9 m above the second collection tray in the absorption column 201 there is the first of 21 further dual-flow trays of the type described above (hole diameter again uniformly 14 mm, but number of holes uniformly 32 020 and opening ratio uniformly 17.4%) which were again arranged equidistantly with a tray spacing of 380 mm. The last of these 21 dual-flow trays is configured as distributor tray having overflow grooves with zig-zag overflow.

800 mm above the last dual-flow tray, the absorption column 201 beings to widen conically. 500 mm above the last dual-flow tray, this widening ends at an internal column diameter of 6.50 m.

At this height, i.e. 1.50 m above the last dual-flow tray, an equidistant (tray spacing =500 mm) arrangement of 28 conventional, single-flow Thormann trays commences. The Thormann trays are configured in such a way that an opposite flow direction of the liquid is achieved in each case in successive grooves in the crossflow direction by the arrangement of the driving slits in the caps of the Thormann trays.

The opening ratio of the Thormann trays is 14%. The ratio of chimney area to slit exit area is 0.8. The chimney height and the height of the discharge weir is 40 mm. The tray freedom of the bubble cap (distance between lower edge of slit and tray) is 10 mm. The slit height is 15 mm. The angle between flared slit and longitudinal edge of the cap is 30° C. The length of the longitudinal edge of the cap is not more than 800 mm. In the peripheral region of the column, the cap length decreases down to 200 mm in order to adapt to the roundness of the column. The distance between two caps located on one line in the cross-sectional direction is 66 mm. The downflow area of the downcomer shaft is 1.5% based on the cross-sectional area of the tray. The width between the two lower longitudinal edges of a cap is 64 mm.

At the level of the uppermost Thormann tray, the separation column again begins to narrow conically. 700 mm above the uppermost Thormann tray, this narrowing is at an end and the internal diameter of the column decreases again to 6.00 m.

1.70 m above the uppermost Thormann tray there is the third collection tray (chimney tray having 16 approximately uniformly distributed roofed chimneys, chimney height=1.50 m).

533 818 kg/h of acidic water having a temperature of 68.6° C. are taken off at a pressure of 1.24 bar from the third collection tray. The composition of the acidic water is:
12.23% by weight of acrylic acid,
4.00% by weight of acetic acid,
78.72% by weight of water,
0.70% by weight of formic acid,
0.09% by weight of formaldehyde,
0.01% by weight of acrolein,
0.01% by weight of propionoic acid,
0.0016% by weight of furfurals,
0.01% by weight of allyl formate and
4.23% by weight of methylene glycol.

29 821 kg/h of the acidic water (68.6° C.) taken off are recirculated together with the inhibitor solution 2 to the uppermost Thormann tray.

60 kg/h of the inhibitor solution 2 are (viewed from the bottom) recirculated to the $19^{th}$ Thormann tray (at a temperature of 25° C. and a pressure of 1.10 bar).

6828 kg/h of the acidic water taken off are passed to incineration. 392 000 kg/h of the acidic water taken off are recirculated at a temperature of 36.6° C. to the sixth of the valve trays described below (calculated from the bottom).

277 000 kg/h of the acidic water taken off are recirculated at a temperature of 31.4° C. to the uppermost of the valve trays described below.

2300 mm above the third collection tray, there are eleven double-flow valve trays arranged equidistantly (tray spacing=500 mm) in the condensation column. The height of the discharge weir is 35 mm. The opening ratio is 18% and the sum of the downflow areas of the downcomer shafts of two successive valve trays is 10% of the column cross section. W12 valves from Stahl, Del., Viernheim, were used as valves. The pressure at the top of the column is 1.2 bar.

169 164 kg/h of offgas having a temperature of 33.7° C. and the following composition leave the top of the absorption column 201:
0.27% by weight of acrylic acid,
0.09% by weight of acetic acid,
2.79% by weight of water,
0.01% by weight of formic acid,
0.08% by weight of acrolein,
2.52% by weight of $CO_2$,
0.78% by weight of CO,
0.09% by weight of propane,
0.21% by weight of propylene
3.62% by weight of oxygen and
89.54% by weight of nitrogen.

The offgas is heated to 43° C. in an indirect heat exchanger and 94 691 kg/h of this offgas are subsequently conveyed via a circulating gas compressor as diluent gas into the gas-phase oxidation and into the redissociation and 74 473 kg/h of the offgas are passed to incineration.

COMPARATIVE EXAMPLE

The comparative example is carried out essentially in the same way as the example with the difference that no mother acid is introduced at the top of the rectification column and the entire mother acid is conveyed onto the fifteenth tray of an absorption column and the runback to the rectification column being formed by the gas mixture leaving the rectification column being cooled to 61° C. at the top of the rectification column by means of a superposed spray condenser. In this way, 5663 kg/h were condensed out and supplied to the uppermost tray of the rectification column. A stabilizer solution comprising 0.98% by weight of phenothiazine dissolved in pure product were continuously introduced into the spray condenser at a rate of 60 kg/h. The runback liquid condensed out had the following composition:
95.10% by weight of acrylic acid,
0.05% by weight of furfurals,
0.02% by weight of acrolein,
0.03% by weight of formic acid,
0.52% by weight of acetic acid,
4.17% by weight of water,
0.1% by weight of propionoic acid and
0.01% by weight of phenothiazine.

All other process parameters were, if appropriate, kept constant. The measure resulted in the temperature at the bottom of the absorption column being reduced to 123° C. and the runback to the absorption column being decreased to 27 899 kg/h. In the offtake stream from the absorption column, the acetic acid content increased to 0.8% by weight and, as a result, a lower purity of acrylic acid of 99.75% by weight with 0.18% by weight of acetic acid was obtained in the output from the crystallization.

The invention claimed is:

1. A plant for recovering acrylic acid, which comprises:
   an absorption column;
   a dissociation column;
   a crystallization apparatus;
   a first line connected to the dissociation column;
   a second line connecting the absorption column and the dissociation column;
   a third line feeding a substream of a mother acid obtained from crystallization in the crystallization apparatus directly into the dissociation column;
   a fourth line feeding a stream of the mother acid directly from the crystallization apparatus, which splits into a feed line feeding a substream of the mother acid directly into the absorption column and the third line; and
   a fifth line connecting the dissociation column d the absorption column.

2. The plant according to claim 1, further comprising:
   a quenching apparatus for quenching a product gas mixture comprising acrylic acid, which is arranged in the fifth line between the dissociation column and the absorption column.

3. The plant according to claim 1, wherein the plant is integrated into an overall plant for preparing acrylic acid.

4. The plant according to claim 1, wherein the third line directly feeds an uppermost tray of the dissociation column.

5. The plant according to claim 1, wherein the first line feeds the dissociation column at a position below a lowermost tray of the dissociation column.

6. The plant according to claim 1, wherein the second line feeds a middle tray of the dissociation column.

* * * * *

UNITED STATES PATENT AND TRADEMARK OFFICE
CERTIFICATE OF CORRECTION

| | |
|---|---|
| PATENT NO. | : 10,343,969 B2 |
| APPLICATION NO. | : 15/615852 |
| DATED | : July 9, 2019 |
| INVENTOR(S) | : Ulrich Hammon et al. |

It is certified that error appears in the above-identified patent and that said Letters Patent is hereby corrected as shown below:

In the Specification

Column 9, Line 11, "cocurrently" should read -- concurrently --.

In the Claims

Column 16, Line 4, "d" should read -- and --.

Signed and Sealed this
Eighteenth Day of February, 2020

Andrei Iancu
*Director of the United States Patent and Trademark Office*